United States Patent
Khan et al.

(10) Patent No.: US 9,695,431 B2
(45) Date of Patent: Jul. 4, 2017

(54) **PROCESS FOR TRANSFORMATION IN *WITHANIA SOMNIFERA* PLANTS TO INCREASE SECONDARY METABOLITE CONTENT**

(71) Applicant: Council of Scientific and Industrial Research, New Delhi (IN)

(72) Inventors: Bashir Mohammad Khan, Pune (IN); Neha Gupta, Pune (IN); Parth Sanjaykumar Patel, Pune (IN); Poonam Sharma, Pune (IN); Shuchishweta Vinay Kendurkar, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 15/024,863

(22) PCT Filed: Sep. 25, 2014

(86) PCT No.: PCT/IN2014/000619
§ 371 (c)(1),
(2) Date: Mar. 25, 2016

(87) PCT Pub. No.: WO2015/044957
PCT Pub. Date: Apr. 2, 2015

(65) Prior Publication Data
US 2016/0304889 A1    Oct. 20, 2016

(30) Foreign Application Priority Data

Sep. 25, 2013 (IN) .......................... 2824/DEL/2013

(51) Int. Cl.
| | | |
|---|---|---|
| *C12N 15/82* | (2006.01) | |
| *C07K 14/41* | (2006.01) | |
| *C12N 15/84* | (2006.01) | |
| *C07K 14/415* | (2006.01) | |

(52) U.S. Cl.
CPC ........ *C12N 15/8205* (2013.01); *C07K 14/415* (2013.01); *C12N 15/8243* (2013.01)

(58) Field of Classification Search
None
See application file for complete search history.

(56) References Cited

FOREIGN PATENT DOCUMENTS

| | | |
|---|---|---|
| CN | 101955972 | 1/2011 |
| CN | 101955972 A * | 1/2011 |
| WO | WO-2015/044957 | 4/2015 |

OTHER PUBLICATIONS

Grover et al. (Journal of Bioscience and Bioengineering, vol. 115 No. 6, pp. 680-685, (2013)).*
Gupta et al. (Mol. Biol. Rep. (2012) 39: pp. 8803-8812).*
Liau et al. (Plant Cell Rep. (2003) 21: pp. 993-998).*
Abe, Ikuro, et al., "Enzymatic Cyclization of Squalene and Oxidosqualene to Sterols and Triterpenes", *Chem. Rev.*, 93, (1993), 2189-2206.
Baxter, Allan, et al., "Squalestatin 1, a Potent Inhibitor of Squalene Synthase, Which Lowers Serum Cholesterol in Vivo", *The Journal of Biological Chemistry*, 267(17), (1992), 11705-11708.
Bergstrom, J. D., et al., "Zaragozicacids: A family of fungal metabolites that are picomolar competitive inhibitors of squalene synthase", *Proc. Nati. Acad. Sci, USA*, 90, (1993), 80-84.
Devarenne, Timothy, et al., "Molecular Characterization of Tobacco Squalene Synthase and Regulation in Response to Fungal Elicitor", *Archives of Biochemistry and Biophysics*, 349(2), (1998), 205-215.
Gamoh, Keiji, et al., "Stereocontrolled Synthesis of Withanolide D and Related Compounds", *J. Chem. Soc. Perkin Trans. I*, (1984), 449-454.
Grover, Abhinav, et al., "Enhanced withanolide production by overexpression of squalene synthase in *Withania somnifera*", *Journal of Bioscience and Bioengineering*, (2012), 1-6.
Ichikawa, Haruyo, et al., "Withanolides potentiate apoptosis, inhibit invasion, and abolish osteoclastogenesis through suppression of nuclear factor-κB (NF-κB) activation and NF-KB—regulated gene expression", *Mol. Cancer Ther.*, 5(6), (2006), 1434-1445.
Jana, Chandan, et al., "Synthesis of Withanolide A, Biological Evaluation of Its NeuritogenicProperties, and Studies on Secretase Inhibition", *Angew. Chem. Int. Ed.*, 50, (2011), 8407-8411.
Jayaprakasam, Bolleddula, et al., "Growth inhibition of human tumor cell lines by withanolides from *Withania somnifera* leaves", *Life Sciences*, 74, (2003), 125-132.
Karst, Francis, et al., "Ergosterol Biosynthesis in *Saccharomyces cerevisiae*. Mutants Deficient in the Early Steps of the Pathway", *Molec. Gen. Genet*, 154, (1977), 269-277.
Kovganko, N. V., et al., "Advances in the Chemical Synthesis of Withanolides", *Chemistry of Natural Compounds*, 33(2), (1997), 133-145.
Lee, Mi-Hyun, et al., "Enhanced Triterpene and Phytosterol Biosynthesis in *Panax ginseng* Overexpressing Squalene Synthase Gene". *Plant Cell Physiol*. 45(8), (2004), 976-984.
Lu, Hong-Yu, et al., "Ri-mediated Transformation of *Glycyrrhiza uralensis* with a Squalene Synthase Gene (GuSQS1) for Production of Glycyrrhizin". *Plant Mol Biol Rep*, 26, (2008), 1-11.
Mirjalili, Mohammad Hossein, et al., "Steroidal Lactones from *Withania somnifera*, an Ancient Plant for Novel Medicine", *Molecules*, 14, (2009), 2373-2393.
Murthy, Hosakatte N., et al., "Establishment of *Withania somnifera* Hairy Root Cultures for the Production of Withanolide A", *Journal of Integrative Plant Biology*, 50(8), (2008), 975-981.
Roja, G., et al., "Tissue Cultures of *Withania somnvera*: Morphogenesis and Withanolide Synthesis", *Phytotherapy*, 5, (1991), 185-187.

(Continued)

*Primary Examiner* — David T Fox
*Assistant Examiner* — Jared Shapiro
(74) *Attorney, Agent, or Firm* — Schwegman Lundberg & Woessner, P.A.

(57) ABSTRACT

Described herein is a process of genetic transformation in *W. somnifera* by *Agrobacterium tumefaciens* mediated transformation to overexpress squalene synthase gene (WsSQS) encoding WsSQS enzyme that catalyzes the synthesis of squalene from farnesyl pyrophosphate. Increased withanolide level including withaferin-A, withanolide A and B and withanone is attained in transformed plant tissues.

8 Claims, 6 Drawing Sheets

(56) References Cited

OTHER PUBLICATIONS

Figure 1:
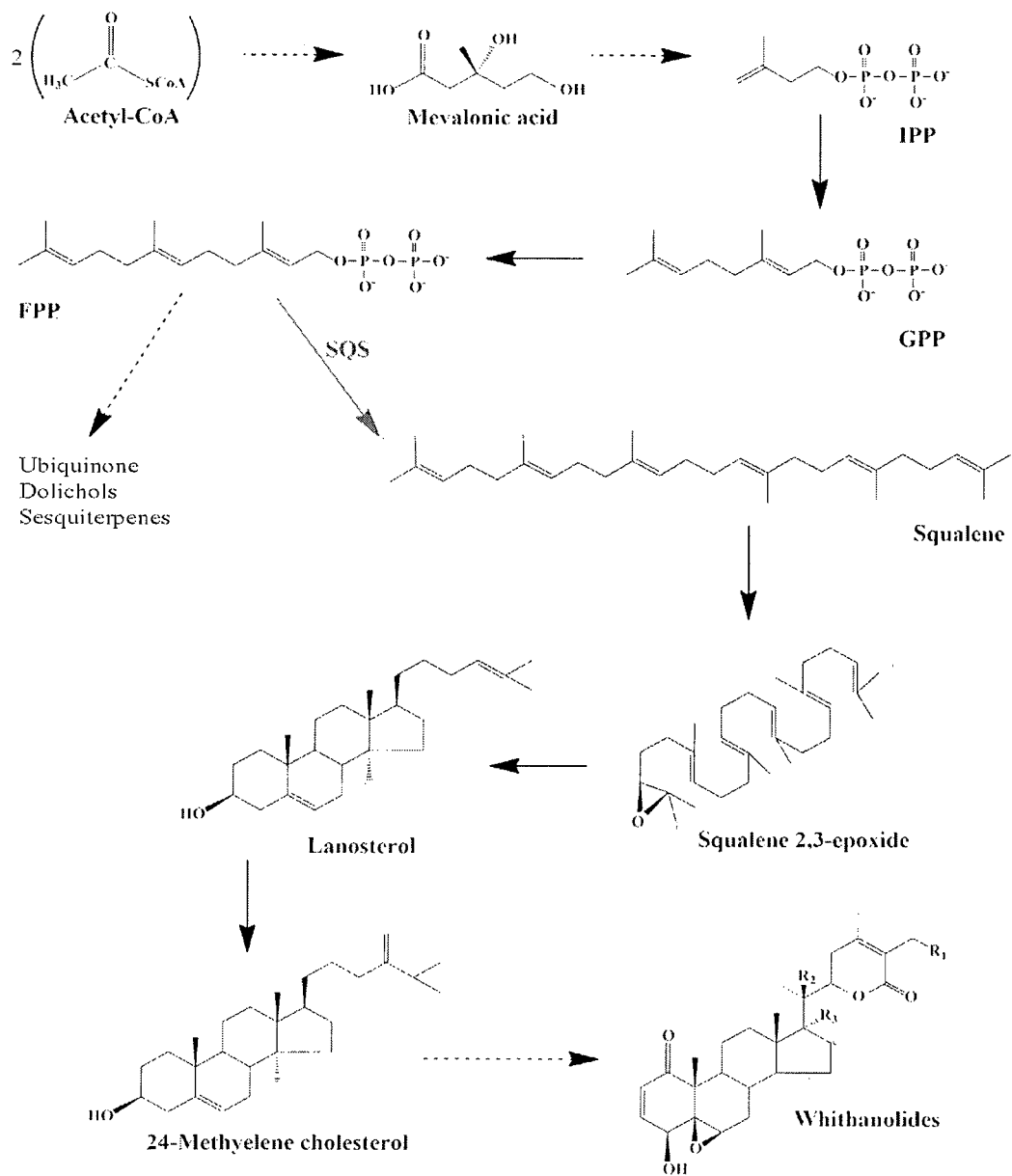

Seo, Jin-Wook, et al., "Overexpression of sgualene synthase in *Eleutheroccous senticosus* increases phytosterol and triterpene accumulation", *Phytochemistry*, 66, (2005), 869-877.
Threlfall, David R., et al., "Co-ordinated inhibition of sgualene synthetase and induction of enzymes of sesguiterpenoid phytoalexin biosynthesis in cultures of *Nicotiana tabacum*", *Phytochemistry*, 27(8), (1988), 2567-2580.
Tohda, Chihiro, et al., "Dendrite extension by methanol extract of Ashwagandha (roots of *Withania somnifera*) in SK-N-SH cells", *NeuroReport*, 11 (2000), 1981-1985.
Tozawa, Ryu-Ichi, et al., "Embryonic Lethality and Defective Neural Tube Closure in Mice Lacking Sgualene Synthase", *The Journal of Biological Chemistry*, 274(43), (1999), 30843-30848.
Vogeli, Urs, et al., "Induction of Sesguiterpene Cyclase and Supression of Squalene Synthetase Activities in Plant Cell Cultures Treated with Fungal Elicitor", *Plant Physiol.*, 88, (1988), 1291-1296.
Wentzinger, Laurent F., et al., "Inhibition of Sgualene Synthase and Squalene Epoxidase in Tobacco Cells Triggers an Up-Regulation of 3-Hydroxy-3-Methylglutaryl Coenzyme A Reductase", *Plant Physiol.*130, (2002), 334-346.
Zhao, Jing, et al., "Withanolide Derivatives from the Roots of *Withania somnifera* and Their Neurite Outgrowth Activities", *Chem. Pharm. Bull.*, 50(6), (2002), 760-765.
"International Application No. PCT/IN2014/000619, International Search Report and Written Opinion mailed Mar. 3, 2015", (Mar. 3, 2015), 11 pgs.
"International Application No. PCT/IN2014/000619, Notification Concerning filing of Article 19 Amendment mailed May 6, 2015", (May 6, 2015), 9 pgs.
Grover, Abhinav, et al., "Enhanced withanolide production by overexpression of squalene synthase in Withania somnifera", Journal of Bioscience and Bioengineering, vol. 115, Issue 6, Jun. 2013, pp. 680-685, (Jun. 2013), 680-685.
Gupta, Neha, et al., "Functional characterization and differential expression studies of squalene synthase from Withania somnifera", Mol Biol Rep (2012) 39:8803-8812, (Jun. 21, 2012), 8803-8812.
Pandey, Vibha, et al., "Agrobacterium tumefaciens-mediated transformation of *Withania somnifera* (L.) Dunal: an important medicinal plant", Plant Cell Rep (2010) 29:133-141, (Dec. 11, 2009), 133-141.

* cited by examiner (a)

(b)

a)

b)

SEQUENCE LISTING

<160> NUMBER OF SEQ ID NOS: 7

<210> SEQ ID NO 1
<211> LENGTH: 1242
<212> TYPE: DNA
<213> ORGANISM: Withania somnifera <300> PUBLICATION INFORMATION:
<308> DATABASE ACCESSION NUMBER: GU732820
<309> DATABASE ENTRY DATE: 2010-10-02
<313> RELEVANT RESIDUES IN SEQ ID NO: (1)..(1242)

<400> SEQUENCE: 1

| | |
|---|---|
| atgggaacat tgagggcgat tttgaagaat ccagatgatt tgtatccatt gataaaacta | 60 |
| aagcttgcgg ctagacatgc ggagaagcag atcccgccgg agccacattg ggccttctgt | 120 |
| tacttaatgc ttcaaaaggt ttctcgtagc tttgctctcg ccattcaaca gcttcctgtt | 180 |
| gagcttcgtg atgctgtatg catattctat ttggttcttc gagcacttga cactgttgag | 240 |
| gatgacacca gcattcccgc agatgttaaa gtaccttattc tgatatcttt tcatcagcat | 300 |
| gtttatgatc gtgaatggca cttttcattg ttaggtggca cgaaggagta caaggttctc | 360 |
| atggaccagt tccatcatgt ttcaaccgct tttctggaac ttgggaaaca ttatcagcag | 420 |
| gcaattcagg atattacctt gaggatgggt gcaggaatgg caaaatttat atgcaaggag | 480 |
| gtggaaacaa ccgatgatta tgacgaatat tgtcactatg tagctgggct tgttggttta | 540 |
| ggattgtcaa aactgtttca tgcctctggg aaggaagatc tggctccaga ttctctctcc | 600 |
| aactctatgg gtttatttct tcagaaaaca aacatcatca gagattattt ggaagacata | 660 |
| aatgaggtgc ccaagtgccg tatgttctgg ccccgtgaga tttggagtaa atatgttaac | 720 |
| aagcttgagg acttaaagta tgaggagaac tcggtcaagg cagtgcaatg cctcaatgac | 780 |
| atggtcacca atgctttgtc acatgtagaa gattgtttga cttacatgtc caatttgcgc | 840 |
| gatcctgcca tctttcgatt ctgtggtatt ccacaggtca tggcaattgg gacattagct | 900 |
| atgtgctacg acaacattga agtcttcaga ggagtggtta aaatgaggcg tggtctgact | 960 |
| gctaaggtca ttgaccggac taggactatg gcagatgtat atggtgcttt ttttgacttc | 1020 |
| tcttgtatgc tgaaatccaa ggttaataat aatgatccaa attcaactaa acgttgaag | 1080 |
| aagcttgaag caatcctgaa aacttgcaga aattcgggaa tgttgaataa aaggaagtct | 1140 |
| tatgtaatca ggagtgagcc aaattacagt ccagttctga ttattgtcat cttcgtcata | 1200 |
| ctggctgtta ttctttcaca actttctggc aaccgatctt ag | 1242 |

<210> SEQ ID NO 2
<211> LENGTH: 22
<212> TYPE: DNA
<213> ORGANISM: Artificial Sequence
<220> FEATURE:
<223> OTHER INFORMATION: Synthetic primer
<220> FEATURE:
<223> OTHER INFORMATION: A synthetic hptII gene specific forward primer sequence

<400> SEQUENCE: 2
tcctgcaagc tccggatgcc tc                                         22

<210> SEQ ID NO 3
<211> LENGTH: 22
<212> TYPE: DNA
<213> ORGANISM: Artificial Sequence
<220> FEATURE:
<223> OTHER INFORMATION: A synthetic hptII gene specific reverse primer sequence

<400> SEQUENCE: 3
cgtgcacagg gtgtcacgtt gc                                         22

```
<210> SEQ ID NO 4
<211> LENGTH: 24
<212> TYPE: DNA
<213> ORGANISM: Artificial Sequence
<220> FEATURE:
<223> OTHER INFORMATION: A synthetic CaMV 35S promoter forward primer
      sequence

<400> SEQUENCE: 4
acagtctcag aagaccaaag ggca                                              24

<210> SEQ ID NO 5
<211> LENGTH: 23
<212> TYPE: DNA
<213> ORGANISM: Artificial Sequence
<220> FEATURE:
<223> OTHER INFORMATION: A synthetic WsSQS gene reverse primer sequence

<400> SEQUENCE: 5
gagctcctaa gatcggttgc cag                                               23

<210> SEQ ID NO 6
<211> LENGTH: 25
<212> TYPE: DNA
<213> ORGANISM: Artificial Sequence
<220> FEATURE:
<223> OTHER INFORMATION: A synthetic WsSQS RT-PCR forward primer
      sequence (SQS-F)

<400> SEQUENCE: 6
tttatgatcg tgaatggcac ttttc                                             25

<210> SEQ ID NO 7
<211> LENGTH: 22
<212> TYPE: DNA
<213> ORGANISM: Artificial Sequence
<220> FEATURE:
<223> OTHER INFORMATION: A synthetic WsSQS RT-PCR reverse primer
      sequence (SQS-R)

<400> SEQUENCE: 7
agcggttgaa acatgatgga ac                                                22
```

PROCESS FOR TRANSFORMATION IN *WITHANIA SOMNIFERA* PLANTS TO INCREASE SECONDARY METABOLITE CONTENT

PRIORITY CLAIM TO RELATED APPLICATIONS

This application is a U.S. national stage application filed under 35 U.S.C. §371 from International Application Serial No. PCT/IN2014/000619, which was filed 25 Sep. 2014, and published as WO2015/044957 on 2 Apr. 2015, and which claims priority to Indian Application No. 2824/DEL/2013, filed 25 Sep. 2013, which applications and publication are incorporated by reference as if reproduced herein and made a part hereof in their entirety, and the benefit of priority of each of which is claimed herein.

FIELD OF THE INVENTION

The present disclosure provides a process for genetic transformation in *Withania somnifera* to produce hardened plants with increased secondary metabolite content. More specifically; the present disclosure relates to genetic transformation in *W. somnifera* plants by *Agrobacterium tumefaciens* to overexpress squalene synthase gene (WsSQS) encoding WsSQS enzyme that catalyzes synthesis of squalene from farnesyl pyrophosphate (FPP). Increased content of secondary metabolites, particularly withanolides are obtained.

BACKGROUND OF THE INVENTION

Isoprenoid biosynthesis is an important cellular metabolic pathway and is responsible for synthesis of structurally diverse and biologically active class of compounds called terpenoids, which includes sterols, steroidal sapogenins, alkaloids and lactones in plants. Withanolides is a group of naturally occurring steroidal lactones commonly present in members of Solanaceae. Majority of secondary metabolites (SMs) concentrated in *Withania somnifera* are responsible for defence, signalling, flavour, fragrance, hormonal, antibiotic, insecticidal, pharmacological and therapeutic efficiencies. *Withania somnifera* (L.) Dunal, commonly known as Indian ginseng, is principally recognized for its medicinal value in Ayurveda. Biological activity of withanolides, especially withanolide A and withaferin A have been studied extensively for their anti-cancerous properties (Jayaprakasam et al. 2003; Ichikawa et al. 2006). Plant extracts from different tissues are found effective in treatment of arthritis, geriatric problems, nervous and venereal disorders. Withanolides have been widely studied for their antioxidant, anti-inflammatory, immunomodulation, antiserotogenic, adaptogenic, rejuvenating effect and for protection against carbon tetrachloride induced hepatotoxicity. Some withanolides have been found associated with dendrite extension (Tohda et al. 2000) and inducing neurite outgrowth in human neuroblastoma SH-SY5Y cells (Zhao et al. 2002).

Withanolides are organic compounds characterized by $C_{28}$ ergostane type steroid backbone and a side chain of C9 units of which a distinctive feature is the six-membered lactone ring which accounts for the plant biological efficacies. The basic skeleton of a withanolide is defined as a 22-hydroxyergostan-26-oic acid-26, 22-lactone and are classified on the basis of their structural variations derived by modifications either on the carbocyclic skeleton or side chain. Currently more than 40 withanolides and several sitoindosides (withanolides with glucose molecule at C-27) have been isolated from aerial parts, roots and berries of *Withania* species.

*Withania somnifera* is a slow growing shrub requiring dry conditions and produces minimal quantity of withanolides which are found to be localized mainly in leaves and roots with concentration ranging from 0.001-0.5% dry weight (Mirjalili et al. 2009). Such miniscule concentrations of withanolides are incapable of accomplishing the tremendously increasing economic demand for medicinal formulations.

Alternatively, chemical synthesis of withanolides have been attempted (Kovganko and Kashkan 1997; Gamoh et al. 1984; Jana et al. 2011), but it requires extensive experimentation due to the structural complexities and specific stereochemical requirements of the compounds resulting in low yield, hence the process is not feasible for secondary metabolite production.

Grover et al (*J Biosci Bioeng*. 2013 June; 115(6):680-5) reports enhanced withanolide production by overexpression of SQS in *Withania somnifera* using *Agrobacterium tumefaciens* as the vector system. Callus cell suspension cultures after transformation were assessed for significant 4-fold increase in squalene synthase activity and 2.5-fold increase in withanolide A content. However, efforts to involve tissue culture techniques in plant biotransformation may result in failure to produce metabolites in sufficient quantity as unorganized tissue cultures are unable to produce secondary metabolites at the same levels as an intact plant. Callus is a chimeric tissue, thus reducing the complete effect of the number of cells actually contributing in withanolide production. The fate of developing cells is also unknown, thus providing no idea about the specific tissue contributing for the production of secondary metabolites There are few reports on plant cell and hairy root cultures developed for the production of the important metabolites from *Withania* extracts (Murthy et al. 2008; Roja et al. 1991), although withanolide production by in vitro cultures is still far from the levels required for economic exploitation. Moreover, an important constraint in the commercial utilization of hairy root culture is development and up-scaling of appropriate vessels for the delicate and sensitive hairy roots.

*Agrobacterium tumefaciens* mediated transformation in *Withania somnifera* plants is performed by Pandey et al, by employing *A. tumefaciens* strain LBA4404, containing binary vector p1G121Hm to obtain transgenic plants. However, absence of a functional gene in the expression vector system and minimum transformation efficiency reduces the applicability of this method.

However, these limitations can be addressed by analysing the biosynthetic pathway of withanolides (described in FIG. 1) and employing genetic engineering as a tool to manipulate crucial steps of the metabolic network to increase the yield of withanolide.

The first committed step which diverts the carbon flux away from the central isoprenoid pathway towards withanolide biosynthesis is squalene formation from farnesyl pyrophosphate (FPP); catalysed by a 47 kDa membrane associated enzyme, squalene synthase (SQS; EC 2.5.1.21) (Abe et al. 1993). The substrate for this enzyme originates from isoprenoid biosynthetic pathway and can be channelled by metabolic engineering towards squalene accumulation which is the first precursor of triterpenoids.

SQS catalyses condensation of two FPP molecules to produce presqualene diphosphate (PSPP) and then converts PSPP to squalene in presence of NADPH and $Mg^{2+}$. Squalene oxidizes in presence of NADPH-linked oxide to afford squalene 2,3-epoxide subsequently cyclizing into lanosterol which serves as a backbone structure for various steroidal triterpenoids. (Mirjalili et al. 2009).

SQS being a regulatory branch point enzyme, has attracted considerable interest as a possible genetic engineering target by blocking a competing branch pathway to promote secondary metabolite biosynthesis in plants. Many approaches have been investigated to understand the regulatory role of SQS in sterol biosynthesis using SQS mutants (Karst and Lacroute, 1977; Tozawa et al., 1999), fungal elicitors (Devarenne et al., 1998; Threlfall and Whitehead, 1988; Vögeli and Chappell, 1988) and specific inhibitors of SQS (Baxter et al., 1992; Bergstrom et al., 1993; Wentzinger et al., 2002). The effect of SQS overexpression on accumulation of SMs were studied in Panax ginseng (Lee et al., 2004) and Eleutherococcus senticosus (Seo et al., 2005), and similar study was also performed in Glycyrrhiza uralensis via Ri-mediated transformation (Lu et al., 2008).

Bearing in mind the minimal concentration of withanolides in plant tissue and the disadvantages posed by chemical synthesis and tissue culture techniques to increase secondary metabolite production in Withania somnifera, the present inventors have developed a transformation process overexpressing WsSQS gene encoding squalene synthase in intact plants of W. somnifera thereby conserving the germplasm of W. somnifera, with considerable increase in withanolide content in all plant tissues.

ABBREVIATIONS

SQS: Squalene synthase
WsSQS: Withania somnifera Squalene synthase
FPP: Farnesyl pyrophosphate
PSPP: Presqualene diphosphate
SM: Secondary Metabolite
MS: Murashige & Skoog medium

SUMMARY OF THE INVENTION

The present disclosure provides a process for genetic transformation in Withania somnifera to produce hardened plants with enhanced secondary metabolite content.

In an aspect, the present disclosure provides a process for transformation in Withania somnifera plants employing an expression vector system carrying WsSQS gene having SEQ ID NO. 1 to cultivate hardened Withania somnifera plants, with increased secondary metabolite content comprising:
a) immersing pre-cultured explants in a bacterial suspension for 10-20 mins and co-cultivating with transformant cells for 24-48 h in dark;
b) transferring cells to proliferation medium containing cefotaxime for ten days;
c) confirming expression of the inserted gene in transformed tissues by Gus assay followed by transferring Gus positive explants to hygromycin B selection medium;
d) maintaining hygromycin B-resistant Gus-positive shoots on selection medium with reduced cefotaxime concentration; and
e) sub-culturing shoots of transformed explants on rooting medium and subjecting transformed plantlets to greenhouse conditions.

Accordingly, Agrobacterium tumefaciens mediated transformation in W. somnifera plants results in overexpression of squalene synthase gene (WsSQS) resulting in enhanced concentration of secondary metabolites.

In another aspect, the present disclosure provides A. tumefaciens harbouring plasmid/binary vector pCAMBIA1301 containing T-DNA construct for W. somnifera plant transformation.

In yet another aspect, the disclosure provides a process of enhancing the yield of withanolides including withaferin-A, withanolide A and B and Withanone from W. somnifera characterized by the transformation process, wherein the transformation process comprises co-cultivating explants with Agrobacterium tumefaciens carrying WsSQS to obtain transformed, hardened W. somnifera plants.

In an aspect, the present disclosure provides a transgenic plant or parts thereof, including seeds comprising a nuclear genome encoded nucleotide sequence as set forth in SEQ ID NO. 1.

In an aspect, the present disclosure provides a cDNA having nucleotide sequence as set forth in SEQ ID NO. 1.

BRIEF DESCRIPTION OF ACCOMPANYING FIGURES

FIG. 1 depicts a simplified scheme of withanolide biosynthetic pathway.

Figure 2:
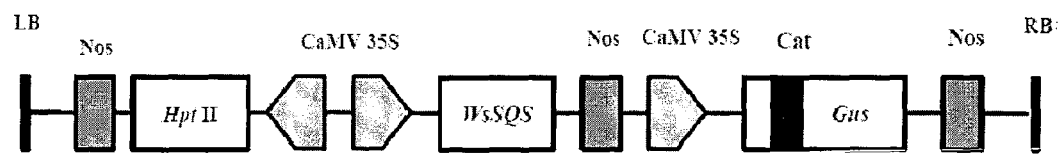

FIG. 2 depicts T-DNA construct prepared and cloned into pCAMBIA 1301 vector for plant transformation. CaMV 35S: Cauliflower mosaic virus 35S rRNA promoter; Nos: Nopaline synthase terminator; Hpt 11: Hygromycin phosphotransferase; WsSQS: W. somnifera squalene synthase; Gus: β-Glucuronidase reporter gene; Cat: Catalase intron; LB: left border; and RB: right border of T-DNA.

Figure 3:
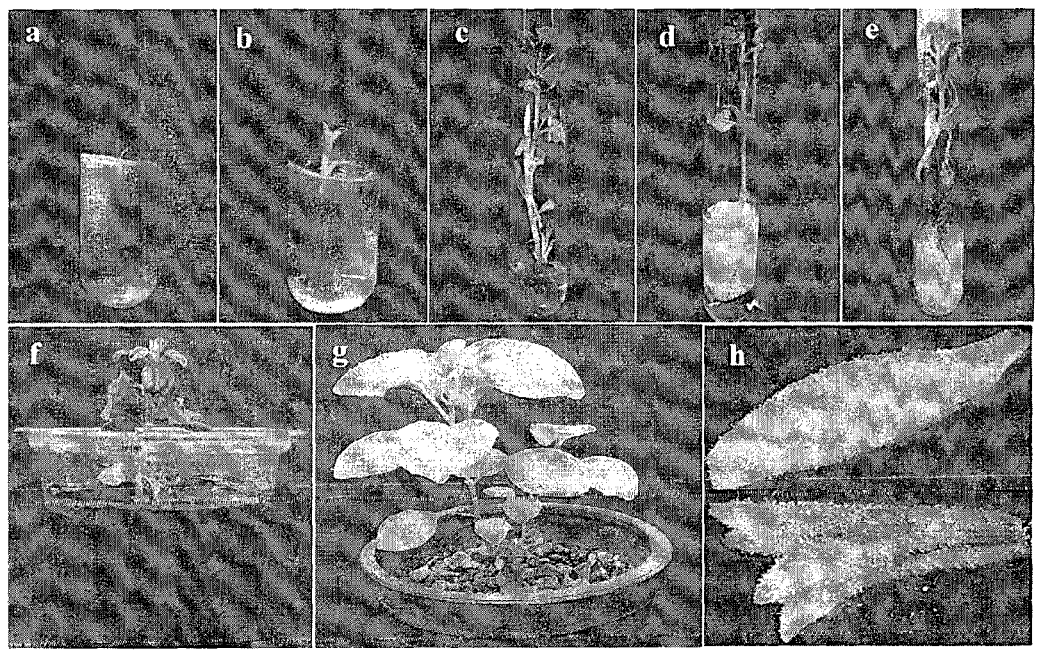

FIG. 3 depicts stages of genetic transformation of W. somnifera. (a) Nodal explant in proliferation media after 2 days of transformation; (b) 10 day old explant in selection media; (c) Shoot elongation and proliferation; (d) Plant transferred in rooting media; (e) Rooted plantlet; (f) Plant transferred in pot; (g) successfully hardened transformed plant in green house; and (h) Gus positive transformed tissues.

Figure 4:
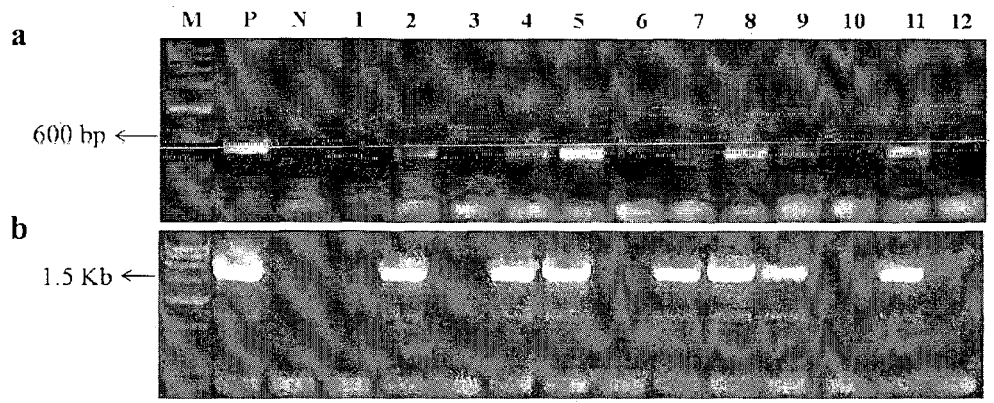

FIG. 4 depicts molecular analysis of different transformed lines. (a) hpt 11 specific PCR showing ~600 bp amplified products; and (b) WsSQS specific PCR showing ~1.6 bp amplified products.

M: Low range molecular weight ladder (Banglore Genei, India); P: Positive control (plasmid pCAMBIA 1301); N: Negative control (untransformed plant); and 1-12: randomly selected putative transformed lines.

Figure 5:
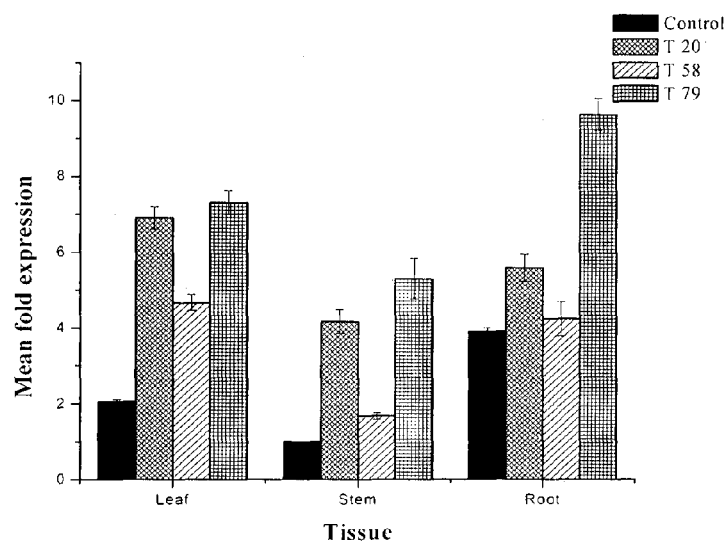

FIG. 5 depicts tissue specific WsSQS transcript analysis in transformed W. somnifera lines by qRT-PCR. Ubiquitin gene was used as an internal control. Tissues from three transformed line (T20, T58 and T79) were used for analysis against the respective untransformed control plant. Values are the means of three replicate measurements and error bars show the standard error of the mean.

Figure 6:
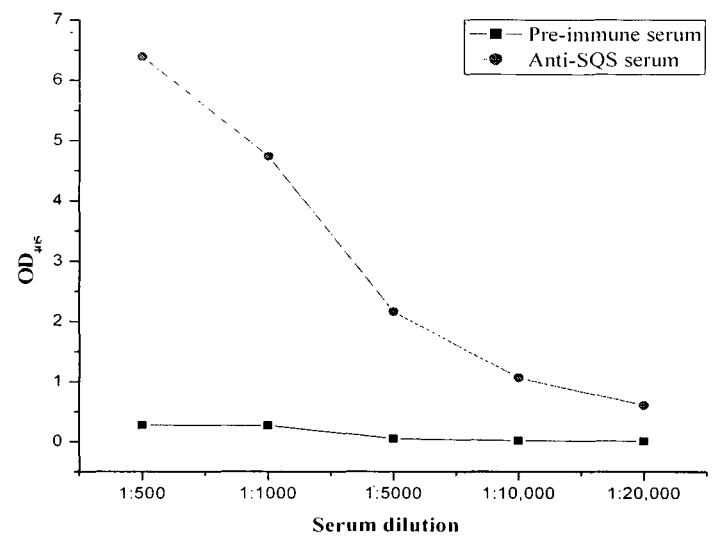
Figure 6:
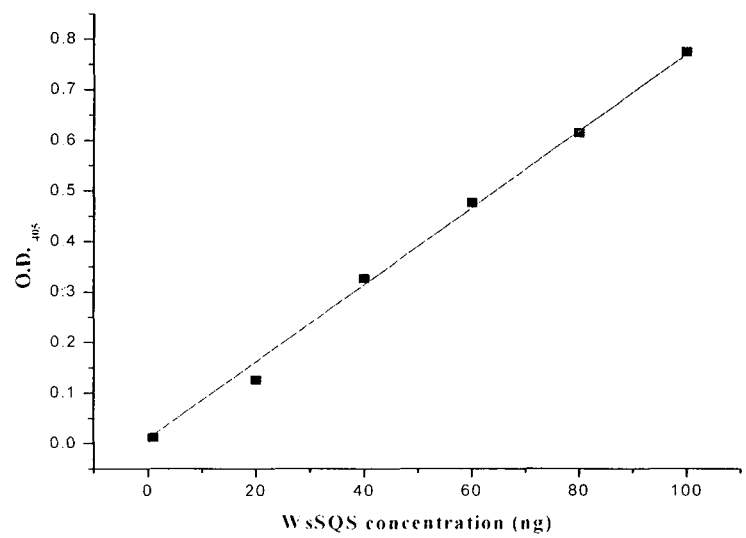

FIG. 6 depicts (a) Determining titre of Anti-WsSQS polyclonal antibody by ELISA, (b) Standard curve of WsSQS for quantification.

Figure 7:
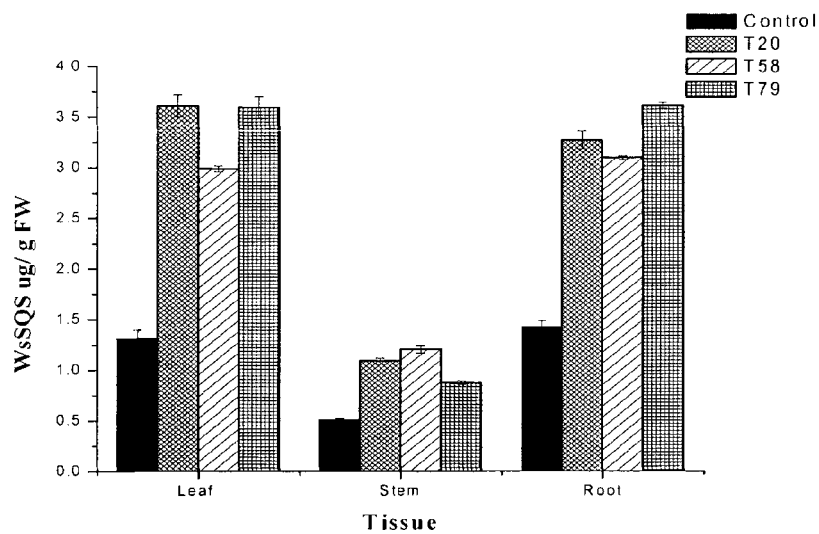
Figure 7:
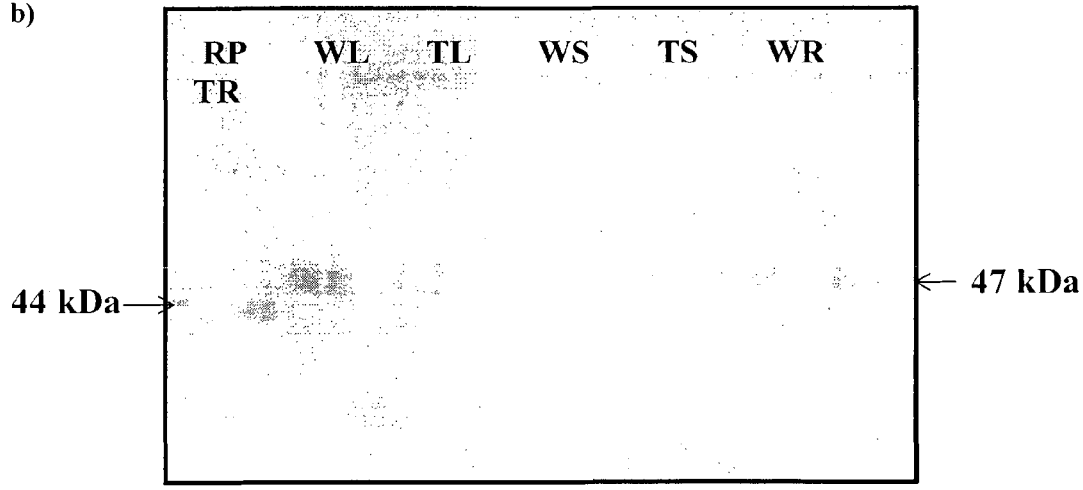

FIG. 7 depicts WsSQS protein expression analysis. (a) WsSQS protein quantification in total soluble protein extracted from different tissues of wild-type and transformed lines by ELISA, determined from the standard curve plotted between purified recombinant WsSQS protein concentration and absorbance at 405 nm; (b) Western blot analysis of W. somnifera transformed with pCAMBIA 1301 harboring WsSQS gene. RC: recombinant truncated WsSQS protein used as size marker; WL: wild-type leaf; TL: Transformed leaf; WS: Wild-type stem; TS: Transformed stem; WR: Wild-type root; and TR: Transformed root.

Figure 8:
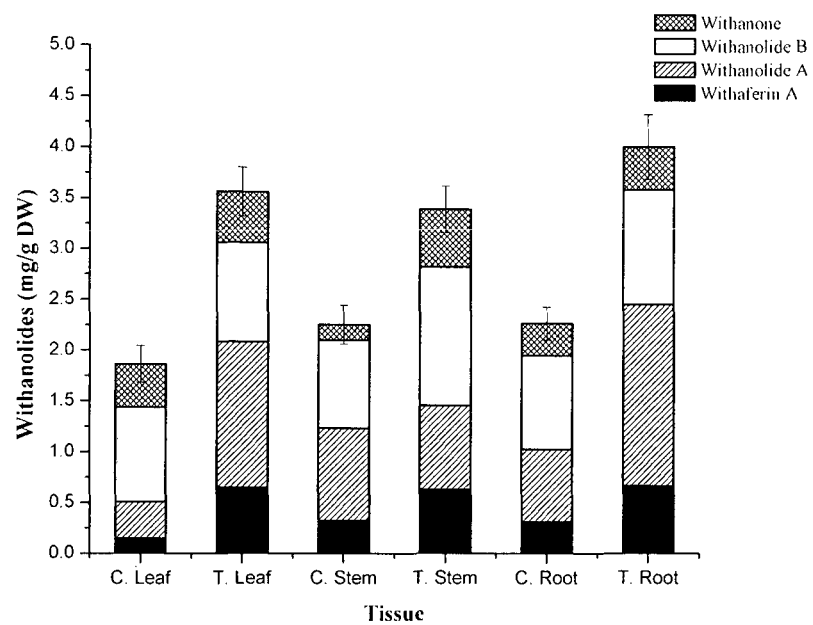

FIG. 8 depicts improved production of withanolides in transformed tissues overexpressing WsSQS. Vertical bars indicate the mean values±SE from three independent experiments.

DETAILED DESCRIPTION OF INVENTION

*Withania somnifera* is traditionally known as 'ashwagandha', and commonly known as Indian ginseng, poison gooseberry, or winter cherry. *Withania somnifera* is cultivated in many of the drier regions of India, such as Mandsaur district of Madhya Pradesh, Punjab, Sindh, Gujarat, and Rajasthan. It is also found in Nepal.

In the present disclosure, the seeds of *W. somnifera* were procured from Vindhya herbals, Bhopal, MP, India. *Agrobacterium tumefaciens* GV2260 is used as the transformation vehicle in the instant disclosure.

The disclosure will now be described in detail in connection with certain preferred and optional embodiments, so that various aspects thereof may be more entirely comprehended and appreciated.

In a preferred embodiment, the present disclosure provides a process for genetic transformation in *Withania somnifera* plants employing an expression vector system carrying WsSQS gene having SEQ ID NO. 1 to cultivate hardened *Withania somnifera* plants, with increased secondary metabolite content comprising:
  a) immersing pre-cultured explants in a bacterial suspension for 10-20 mins and co-cultivating with transformant cells for 24-48 h in dark;
  b) transferring cells to proliferation medium containing cefotaxime for 8-10 days;
  c) confirming expression of the inserted gene in transformed tissues by Gus assay followed by transferring Gus positive explants to hygromycin B selection medium;
  d) maintaining hygromycin B-resistant Gus-positive shoots on selection medium with reduced cefotaxime concentration; and
  e) sub-culturing shoots of transformed explants on rooting medium and subjecting transformed plantlets to greenhouse conditions.

*Agrobacterium tumefaciens* mediated transformation in *Withania somnifera* plants results in the overexpression of squalene synthase gene (WsSQS) encoding the WsSQS enzyme, and thereby causing enhanced catalysis of squalene from farnesyl pyrophosphate.

Accordingly, 80-100 pre-cultured explants are immersed with freshly prepared *A. tumefaciens* suspension for 15 mins followed by co-cultivating with *A. tumefaciens* for 48 h in dark and transferred to proliferation medium containing 220-300 mg $l^{-1}$ cefotaxime for 8-10 days to obtain *A. tumefaciens* mediated transformed cell lines of *W. somnifera*.

In order to establish the expression of the inserted WsSQS gene in the explants, the cells are determined for their glucuronidase (Gus) activity and hygromycin resistant property. Cells exhibiting Gus+ and hygromycin resistance are maintained on selection medium with cefotaxime concentration reduced to 100 mg $l^{-1}$ to eliminate growth of *Agrobacterium*.

Independent transformed lines obtained by detaching shoots from transformed explant are transferred to a rooting medium. Efficient rooting is obtained in appropriate plant growth medium at favourable growth conditions and is transferred to green house for acclimatization In an embodiment, the present disclosure provides a bacterial suspension comprising cells of *A. tumefaciens* harboring plasmid carrying SEQ ID NO. 1, wherein precultured explants are co-cultivated with the said bacterial suspension.

In an embodiment, the present disclosure provides a transgenic plant or parts thereof, including seeds comprising a nuclear genome encoded nucleotide sequence as set forth in SEQ ID NO. 1.

In an embodiment, the present disclosure provides a cDNA having nucleotide sequence as set forth in SEQ ID NO. 1.

In another preferred embodiment, the present disclosure provides an expression vector system *A. tumefaciens* harbouring pCAMBIA 1301 containing the T-DNA construct comprising (described in FIG. 2)
  a) positioning WsSQS cDNA fragment between cauliflower mosaic virus (CaMV) 35S as the promoter and nopaline synthase (Nos) terminator in modified pCAMBIA 1301 vector, and
  b) gus (β-Glucuronidase) reporter gene with catalase intron and a selectable marker hpt II (hygromycin phosphotransferase) gene imparting resistance against hygromycin B.

Accordingly, cloned cDNA WsSQS fragments of SEQ ID NO: 1 (Accession No: GU732820) with opening reading frame of 1242 bp, were obtained by amplification using primers consisting of restriction enzymes sites KpnI and SacI. The WsSQS open reading frame is adjusted between CaMV 35S promoter and Nos terminator using site specific restriction enzymes to ensure high levels of gene expression.

Accordingly *A. tumefaciens* characterized by WsSQS gene is grown in yeast extract minimal medium containing rifampicin and kanamycin in 1:1 ratio. Cells harvested by centrifugation are resuspended in MS medium to obtain suitable bacterial cell density for infection. 90 explants which are two days pre-cultured apical and nodal segments from in vitro grown shoots as explants are initially immersed with freshly prepared *A. tumefaciens* suspension for 15 mins followed by co-cultivating with *A. tumefaciens* for 48 h in dark and transferred to cefotaxime containing proliferation medium for ten days to obtain *A. tumefaciens* mediated transformed cell lines of *W. somnifera*.

Further, expression of WsSQS gene in transformed tissues is confirmed by Gus assay to detect β-Glucuronidase activity according to Jefferson et al., 1987 and by growing Gus+ transformants on hygromycin B selective medium. Hygromycin B-resistant, Gus-positive shoots are continuously maintained on selection medium with cefotaxime concentration reduced to 100 mg $l^{-1}$.

Independent transformed lines obtained by detaching shoots from transformed explant are transferred to rooting medium. Efficient rooting is obtained in appropriate plant growth medium at favourable growth conditions and is transferred to green house for acclimatization.

Accordingly expression of introduced gene is determined by β-glucuronidase activity in explants. Gus reporter gene with catalase intron does not express detectable Gus activity in *A. tumefaciens*; however transformed Gus-positive shoots stained blue indicate stable expression of the introduced gene.

Gus+ transformants grown in proliferation medium containing 10 mg$l^{-1}$ hygromycin B as the selective antibiotic exhibit shoot elongation and multiplication while untransformed tissues are indicated by necrotic shoots are eliminated. Growth of Gus+, hygromycin B resistant transformed cell lines are sustained in selection medium with decreased concentration of cefotaxime.

Consequently, of the 90 explants subjected to transformation, a total of 18 hygromycin B resistant transformed lines are recovered. Green shoots are subsequently cultured onto rooting medium. Rooted plants are transferred to pots containing autoclaved sand and soil (1:2), kept in humid conditions for two weeks and are then shifted to green house for further acclimatization.

In yet another embodiment transformed, hardened *W. somnifera* plants with increased withanolide content are obtained. Transgenic plants thus obtained are normal in growth with no phenotypic aberrations.

Randomly selected transformed lines T20, T58 and T79 exhibit increased mRNA transcript levels up to 2-5 fold as compared to the respective wild-type tissue. Favourably, the transcriptionally activated WsSQS gene catalysing the regulatory step leading to withanolide biosynthesis was up regulated in all the transformed tissues.

Advantageously WsSQS activity in transformed leaf and stem tissues was found to be 2.7 and 2.1 fold higher, respectively, while it was 3.3 fold higher in case of root tissue compared to wild type tissues. The increase in WsSQS activity is transformed cell lines compared to wild type tissue is described in Table 1.

In accordance with Western blot analysis the increased intensity of the immune-precipitated protein bands of transformed tissues confirms that WsSQS protein detected in the transformed lines is the product of the overexpressed WsSQS coding region.

TABLE 1

Summary of WsSQS activity and squalene detected in the reactions

| Plant Tissue | Sample | WsSQS activity (pKat/mg protein) | WsSQS activity (pKat/g FW) | Squalene (μmol/mg protein) |
|---|---|---|---|---|
| Leaf | Wild type Leaf | 36 | 0.72 | 54 |
|  | Transformed Leaf | 54.7 | 1.98 | 82 |
| Stem | Wild type Stem | 10 | 0.39 | 15 |
|  | Transformed Stem | 14.4 | 0.83 | 23 |
| Root | Wild Type Root | 41 | 0.82 | 57 |
|  | Transformed Root | 139.4 | 2.78 | 180 |

Further, the WsSQS activity in the transformed plant tissues is in the range of 50-150 pKat/mgprotein. (Refer Table 1)

In yet another preferred embodiment enhanced concentrations of withanolide secondary metabolites including withaferin A, withanolide A and B and withanone are obtained.

LC-ESI-MS provides identification of Withaferin A, Withanolide A, Withanolide B and Withanone characterised by retention time (Rt) and mass spectrum facilitates their quantification.

Values represent the mean of three independent experiments with their SD and expressed as mg/g DW of the respective tissue.

The disclosure will now be illustrated with help of examples. The aforementioned embodiments and below mentioned examples are for illustrative purpose and are not meant to limit the scope of the disclosure. Various modifications of aforementioned embodiments and below mentioned examples are readily apparent to a person skilled in the art. All such modifications may be construed to fall within the scope and limit of this disclosure as defined by the appended claims.

EXAMPLES

Example 1

Plant Material and Propagation

Seeds of *W. somnifera* were procured from Vindhya herbals, Bhopal, MP, India. Seeds were surface sterilized with sterile distilled water and then rinsed with 1% (v/v) teepol for 1 min followed by sterile distilled water washings in laminar air flow cabinet. Seeds were then treated with 0.1% (w/v) mercuric chloride ($HgCl_2$) for 5 min, washed thoroughly with sterile distilled water to remove traces of $HgCl_2$. Seeds were inoculated on germination medium (half strength MS medium containing 3% (w/v) sucrose and solidified with 0.3% Phytagel) and incubated in dark for 15 days to germinate. Germinated seeds were transferred to liquid half strength MS medium for further seedling development. Seedlings were cut into apical and nodal segments of about 1 cm length containing a single node along with a small portion of petiole and micropropagated by inoculating into the proliferation medium (MS medium supplemented with 0.1 mg $l^{-1}$ kinetin, 0.2 mg $l^{-1}$ 6-BAP) for shooting and subsequently transferred to rooting medium (half-strength MS liquid medium containing 2 mg $l^{-1}$ IBA) to develop into complete plants. Cultures were incubated under 60 μmol $m^{-2}s^{-1}$ light intensity at 26+2° C. for 16 h photoperiod. Apical and nodal segments from in vitro grown shoots were used as explants for transformation.

Example 2

Vector Construction

Previously cloned full length WsSQS (GenBank GU732820) with an open reading frame of 1242 bp (SEQ ID NO. 1) was amplified using primers having sites for restriction enzymes KpnI and SacI. The resulting fragment was positioned between cauliflower mosaic virus (CaMV) 35S and a nopaline synthase (Nos) terminator in modified pCAMBIA 1301 vector (Omer et al., 2013) which had been already digested with the same enzymes. The correct orien-

TABLE 2

Quantitative determination of different withanolide content by LC-MS in leaf, stem and root of transformed *W. somnifera* overexpressing WsSQS

| Withanolides | $R_t$ (min) | Leaf | | Stem | | Root | |
|---|---|---|---|---|---|---|---|
|  |  | Wild-type | Transformed | Wild-type | Transformed | Wild-type | Transformed |
| Withaferin A | 11.31 | 0.15 ± 0.012 | 0.65 ± 0.09 | 0.32 ± 0.04 | 0.63 ± 0.07 | 0.31 ± 0.05 | 0.66 ± 0.08 |
| Withanolide A | 12.35 | 0.35 ± 0.03 | 1.43 ± 0.12 | 0.91 ± 0.09 | 0.82 ± 0.08 | 0.71 ± 0.09 | 1.78 ± 0.16 |
| Withanolide B | 15.00 | 0.92 ± 0.10 | 0.98 ± 0.09 | 0.86 ± 0.07 | 1.36 ± 0.18 | 0.92 ± 0.12 | 1.12 ± 0.14 |
| Withanone | 18.35 | 0.42 ± 0.06 | 0.49 ± 0.08 | 0.15 ± 0.016 | 0.56 ± 0.05 | 0.31 ± 0.04 | 0.42 ± 0.07 | tation within the vector was confirmed by DNA sequencing and the construct was transformed into *A. tumefaciens* GV2260. The T-DNA region of the vector was constituted by gus (β-Glucuronidase) reporter gene and a selectable marker hpt II (hygromycin phosphotransferase) gene imparting resistance to hygromycin B under the control of the constitutive CaMV 35S promoter (FIG. 2).

Example 3

Genetic Transformation of *W. somnifera*

Genetic transformation in *W. somnifera* was achieved by *A. tumefaciens* GV2260 carrying WsSQS. *A. tumefaciens* was grown in yeast extract minimal medium containing 50 mg $l^{-1}$ rifampicin and 50 mg $l^{-1}$ kanamycin, harvested by centrifugation and the bacterial pellet was resuspended in MS medium to obtain appropriate bacterial cell density for infection. Two days pre-cultured explants were immersed in freshly prepared bacterial suspension for 15 min and co-cultivated with *A. tumefaciens* for 48 h in dark and then transferred to a proliferation medium containing 250 mg $l^{-1}$ cefotaxime for ten days. Expression of the inserted gene in transformed tissues was confirmed by Gus assay to detect the β-Glucuronidase activity (Jefferson et al., 1987) and visualizing it under a stereoscope (Leica MZ 125, Switzerland). Explants exhibiting shoot development were then transferred to selection medium (proliferation medium containing 10 mg $l^{-1}$ hygromycin B). Hygromycin B-resistant Gus-positive shoots were continuously maintained on selection pressure while cefotaxime concentration was decreased to 100 mg $l^{-1}$. To produce independent transformed lines, shoots were detached from the transformed explant, cultured on proliferation medium and rooted onto rooting medium. Rooted plants were shifted to plastic pots containing autoclaved sand and soil (1:2), kept covered with plastic sheets to maintain humidity for two weeks and then transferred to green house for further acclimatization.

Example 4

Molecular Identification of Transformants by PCR Analysis

Presence of integrated DNA into genome of transformed tissues was confirmed by PCR (C1000 BIO-RAD thermal cycler, USA) using primers specific to hpt II and WsSQS. Total genomic DNA was extracted from tissues of wild-type and hygromycin B-resistant transformed shoots by using plant DNA extraction kit (Hipura Plant Genomic Purification kit, Himedia, India). The hpt II gene specific forward and reverse primer sequences used were (SEQ ID NO. 2) 5'-TCCTGCAAGCTCCGGATGCCTC-3' and 5'-CGTGCACAGGGTGTCACGTTGC-3' (SEQ ID NO. 3) respectively.

For WsSQS gene specific PCR, the forward primer was designed from the sequence of CaMV 35S promoter (GeneBank GQ336528.1; 5'-ACAGTCTCAGAAGAC-CAAAGGGCA-3') (SEQ ID NO. 4) and reverse primer was designed from the 3' terminal sequence of WsSQS (GeneBank GU732820; 5'-GAGCTCCTAAGATCGGTTGC-CAG-3') (SEQ ID NO. 5). Components of PCR reaction mixture were: 15 ng template DNA, 150 μM dNTPs, hpt II/SQS gene specific forward and reverse primers (0.66 pmol each), 0.5 U of Taq DNA polymerase in a total volume of 15 μl with 1× reaction buffer. The PCR reaction was carried out as follows: an initial denaturation at 94° C. for 5 min followed by 35 cycles of denaturation at 94° C. for 30 s, annealing at 55° C. for 30 s and extension at 72° C. for 1 min (for hpt II) and 1.6 min (for WsSQS) and a final 5 min extension at 72° C. The amplified products were subjected to 1% (w/v) agarose gel electrophoresis and visualized by ethidium bromide staining under UV. (Observed in FIG. 4.)

Example 5 qRT-PCR Analysis

Total RNA was isolated from different tissues (leaf, stem and root) of transformed lines and wild-type *W. somnifera* using Plant RNA Isolation Kit (Invitrogen) as per manual instructions and treated with DNase using DNase I Digest kit (Sigma, USA) to eliminate DNA contamination. Total RNA (2 μg) was reverse transcribed into cDNA using AMV reverse transcription system (Promega, USA) with oligo dT primers in a 20 μL reaction volume. The reaction mixture was incubated for 1 h at 42° C. For normalization of the relative expression data, ubiquitin gene was employed as an internal standard using primer mix from Eurogentec (Belgium). To quantify WsSQS transcripts, first-strand DNA was PCR amplified using gene-specific primers: SQS-F (5'-TTTATGATCGTGAATGGCACTTTTC-3') (SEQ ID NO. 6) and SQS-R (5'-AGCGGTTGAAACATGATGGAAC-3') (SEQ ID NO. 7) synthesized from WsSQS. All qRT-PCR reactions were performed with SYBR Green Brilliant® II QPCR Master Mix (2× with low ROX, Stratagene, USA) on Mx 3000P instrument (Stratagene, USA) according to the manufacturer's instructions. PCR cycling conditions included a DNA denaturing stage of 95° C. for 10 min, followed by 40 cycles of 95° C. for 30 s, 55° C. for 45 s and 72° C. for 30 s. The amplified products were analyzed with MxPro software provided with the machine. Data was analyzed by comparative Ct method (Pfafll, 2001).

Example 6

Indirect ELISA and Western Blot of WsSQS Protein

Fresh tissues (500 mg each) of transformed and wild-type plants were ground in liquid nitrogen and resuspended in 1 ml phosphate buffered saline (PBS; 136 mM NaCl, 2 mM KCl, 8 mM $Na_2HPO_4$, 1 mM $KH_2PO_4$, pH 7.5) containing CHAPS (5 mM) to solubilize membrane proteins. The supernatant was collected after centrifugation and the total protein quantity was estimated by Bradford assay, using bovine serum albumin as standard. Antibodies against WsSQS raised in rabbits (New Zealand White) and the antibody titre of the anti-SQS serum were determined by plotting a graph of different antisera dilution (1:500, 1:1000, 1:5000, 1:10000 and 1:20000) against recombinant truncated WsSQS. For detection of WsSQS in total plant protein, the equal concentration of extracted protein (100 μL/well) was coated on 96 well polystyrene microtitre plate (Costar, USA) for overnight at 4° C. followed by washings with PBST (PBS+0.05% Tween 20). Non-specific sites were blocked with blocking buffer (PBS+1% BSA) and incubated for 2 h at 37° C. After washing thrice with PBST, primary antibody (1:5000 dilution) was added and incubated for 2 h at 37° C. Unbound primary antibody was washed thrice with PBST and the plate was exposed to secondary antibody (goat anti-rabbit IgG-alkaline phosphatase conjugate, 1:20000) and followed by incubation for 1-2 h at 37° C. The presence of antigen was determined by the addition of enzyme specific substrate pNPP (p-Nitro phenyl phosphate; 1 mg/mL) followed by incubation of 45 min in dark for color development. The reaction was terminated by adding 10 mM EDTA and absorbance was measured at 405 nm using an xMark ELISA plate reader (BIO-RAD, USA). Detection limit of ELISA was determined by plotting a standard curve using the purified recombinant truncated WsSQS protein. Concentration of WsSQS present in total soluble protein extracted from wild-type and transformed plants were analyzed in each case of three replications from the standard curve.

Total crude protein (50 μg) from transformed and wild-type tissues was electrophoresed on 10% SDS-PAGE and electro-transferred on to PVDF membrane using iBlot gel transfer system (Invitrogen) as per manufacturer's instructions, with recombinant truncated WsSQS used as a size marker. Western Breeze kit (Invitrogen) was used for further processing of the blot. Blot was placed in blocking solution and incubated at room temperature for 30 min on rotatary shaker. The membrane was rinsed and incubated with primary antibody solution (1:5000 dilution, rabbit polyclonal IgG against WsSQS) for 1 h. The membrane was washed thrice and incubated in secondary antibody for 30 min. Signals were detected with ready to use 5-bromo-4-chloro-3-indolyl phosphate and nitroblue tetrazolium (BCIP/NBT) solution (Calbiochem, Germany) (Harlow and Lane, 1988).

Example 7

WsSQS Enzyme Activity Determination

Microsomal protein fractions were prepared for WsSQS activity measurements from different tissues of the transformed and wild-type plants. (Vögeli and Chappell, 1988). Essentially, 1 g frozen tissue was homogenized in 10 mL protein extraction buffer (PBS, pH 7.5, 1% PVP, 5 mM DTT and 0.5 M sucrose). Homogenates were filtered through 40 μm mesh and centrifuged at 10,000 g for 25 min at 4° C. The supernatant was again centrifuged at 100,000 g for 60 min to obtain the microsomal pellet which was resuspended in 200 μL of 100 mM Tris Cl (pH 7.5), 1.5 mM DTT and 20% glycerol and protein concentration was determined by Bradford method. Assay for WsSQS enzyme was carried out with 10 μg microsomal protein according to the method described previously (Gupta et al., 2012).

Enzyme Activity Determination by Fluorimetry

Enzyme activity was determined flourimetrically by measuring NADPH depletion during the reaction on an LS 55 spectrofluorimeter (Perkin Elmer). Assay mixture was excited at 340 nm and emission was recorded in the range 400-500 nm with characteristic maxima around 460 nm corresponding to NADPH fluorescence. Excitation and emission slits were kept at 7.5 and 2.5 nm, respectively, with a scan speed of 100 nm min$^{-1}$. The reaction was carried out at 30° C. for 1 h and averaged fluorescence of 5 accumulated scans were recorded at regular time intervals. A standard curve was prepared by plotting fluorescence of commercially available NADPH (dissolved in 50 mM Tris-Cl; pH 8.0) at 460 nm against its different concentrations. Enzyme activity was defined as the pKat/mg protein.

Enzyme Activity Determination by GC-MS

In order to validate the enzyme reactions, squalene formed in each reaction was checked on GC-MS. Replicates of the above mentioned reactions, after 2 h of incubation, were extracted using tert-butyl methyl ether and concentrated to 100 μL by bubbling dry nitrogen. The concentrate (1 μL) was injected on GC-MS (Agilent 5975C mass selective detector interfaced with an Agilent 7890A gas chromatograph) fitted with a capillary column HP-5 (25 m×0.25 mm, film thickness 0.33 μm 5% methyl polysiloxane cross-linked capillary column, Hewlett-Packard, USA) with a split ratio of 10:1. The injector temperature was set at 290° C. with helium as the carrier gas (10 mL min$^{-1}$). The oven temperature was programmed from 150° C. to 250° C. at 10° C. min$^{-1}$ and from 250° C. to 310° C. at the rate of 5° C. min$^{-1}$, and maintained at final temperature for 5 min. The chromatogram obtained was compared with standard/commercially available squalene (Sigma, USA) for its retention time and mass fragmentation pattern. The squalene content was calculated from the standard curve plotted from the peak area versus concentrations of standard squalene, and expressed in nmol/mg protein.

Example 8

Withanolides Extraction and LC-ESI-MS Analysis

Dried tissues (100 mg each) were separately crushed to fine powder and percolated thrice with 5 ml methanol for 1 h under shaking conditions at room temperature. Extracts were pooled, filtered, concentrated under reduced pressure at 45° C. and thoroughly washed with equal volume of n-hexane. The methanol fraction was dried completely and further partitioned twice with water:chloroform (1:1). The chloroform fractions were pooled, concentrated and finally dissolved in 150 μl methanol. The samples were filtered and subjected to liquid chromatography. All the solvents used in the study were HPLC grade purchased from Fischer Scientific, USA.

LC-MS was performed on Waters Acquity UPLC system (Milford, Mass., USA) with an Acquity UPLC® BEH C18 column (2.1×100 mm, 1.7 μm) attached to a positive ion elecrospray ionization-mass spectrometer (Waters) for identification and quantification of withanolides in *W. somnifera* extracts. Separations were achieved following a binary gradient elution using water (solvent A) and acetonitrile (solvent B) with the following program carried out at 25° C.: 10% B for 2 min; 45% B for 8 min; 75% B for 10 min; and 95% B for 5 min, at a flow-rate of 0.4 mL/min, with a total run time of 25 min. External standards of different withanolides (Chromadex, USA) were used to construct calibrated graph from peak area versus withanolide concentration, being linear over 10 measurements at different concentrations.

Sequence Listing

| SEQ ID NO. | Sequence Length | Description | Sequence | | | |
|---|---|---|---|---|---|---|
| SEQ ID NO. 1 | 1242 bp | DNA sequence Plant: Withania somnifera | atgggaacat tgtatccatt ggagaagcag tacttaatgc ccattcaaca catattctat gatgacacca tgatatcttt cttttcattg atggaccagt | tgagggcgat gataaaacta atcccgccgg ttcaaaaggt gcttcctgtt ttggttcttc gcattcccgc tcatcagcat ttaggtggca tccatcatgt | tttgaagaat aagcttgcgg agccacattg ttctcgtagc gagcttcgtg gagcacttga agatgttaaa gtttatgatc cgaaggagta ttcaaccgct | ccagatgatt ctagacatgc ggccttctgt tttgctctcg atgctgtatg cactgttgag gtacctattc gtgaatggca caaggttctc tttctggaac |

Sequence Listing-continued

| SEQ ID NO. | Sequence Length | Description | Sequence |
|---|---|---|---|
| | | | ttgggaaaca ttatcagcag gcaattcagg atattacctt |
| | | | gaggatgggt gcaggaatgg caaaatttat atgcaaggag |
| | | | gtggaaacaa ccgatgatta tgacgaatat tgtcactatg |
| | | | tagctgggct tgttggttta ggattgtcaa aactgtttca |
| | | | tgcctctggg aaggaagatc tggctccaga ttctctctcc |
| | | | aactctatgg gtttatttct tcagaaaaca aacatcatca |
| | | | gagattattt ggaagacata aatgaggtgc ccaagtgccg |
| | | | tatgttctgg ccccgtgaga tttggagtaa atatgttaac |
| | | | aagcttgagg acttaaagta tgaggagaac tcggtcaagg |
| | | | cagtgcaatg cctcaatgac atggtcacca atgctttgtc |
| | | | acatgtagaa gattgtttga cttacatgtc caatttgcgc |
| | | | gatcctgcca tctttcgatt ctgtggtatt ccacaggtca |
| | | | tggcaattgg gacattagct atgtgctacg acaacattga |
| | | | agtcttcaga ggagtggtta aaatgaggcg tggtctgact |
| | | | gctaaggtca ttgaccggac taggactatg gcagatgtat |
| | | | atggtgcttt ttttgacttc tcttgtatgc tgaaatccaa |
| | | | ggttaataat aatgatccaa attcaactaa aacgttgaag |
| | | | aagcttgaag caatcctgaa aacttgcaga aattcgggaa |
| | | | tgttgaataa aaggaagtct tatgtaatca ggagtgagcc |
| | | | aaaattacagt ccagttctga ttattgtcat cttcgtcata |
| | | | ctggctgtta ttctttcaca actttctggc aaccgatctt |
| | | | ag |
| SEQ ID NO. 2 | 22 bp | PrimerF hptII gene specific forward primer sequence | tcctgcaagc tccggatgcc tc |
| SEQ ID NO. 3 | 22 bp | PrimerR hptII gene specific reverse primer sequence | cgtgcacagg gtgtcacgtt gc |
| SEQ ID NO. 4 | 24 bp | CaMV 35S promoter forward primer sequence | acagtctcag aagaccaaag ggca |
| SEQ ID NO. 5 | 23 bp | DNA sequence WsSQS gene reverse primer sequence | gagctcctaa gatcggttgc cag |
| SEQ ID NO. 6 | 25 bp | DNA sequence WsSQS RT-PCR forward primer sequence (SQS-F) | tttatgatcg tgaatggcac tttc |
| SEQ ID NO. 7 | 22 bp | DNA Sequence WsSQS RT-PCR reverse primer sequence (SQS-R) | agcggttgaa acatgatgga ac |

We claim:

1. A process for genetic transformation in *Withania somnifera* plants to increase secondary metabolite content in green house acclimatized plants, comprising:
   a) immersing a pre-cultured *Withania somnifera* explant in a bacterial suspension comprising an *Agrobacterium tumefaciens* harboring a plasmid carrying a cDNA sequence of squalene synthase (WsSQS) comprising SEQ ID NO: 1 for 10-20 mins and co-cultivating the pre-cultured explant and the *Agrobacterium* for 24-48 h in dark;
   b) transferring the co-cultivated explant to a proliferation medium containing cefotaxime for 8-10 days so as to provide a tissue;
   c) determining Gus expression in the tissue by Gus assay followed by transferring Gus positive tissue to hygromycin B selection medium, thereby providing shoots;
   d) maintaining the shoots on hygromycin B while reducing the concentration of cefotaxime; and
   e) transferring the shoots to rooting medium to provide transformed plantlets and subjecting the transformed plantlets to greenhouse conditions;
   wherein the explant is an apical or nodal segment from a seedling shoot.

2. The process for genetic transformation according to claim 1, wherein the plasmid carrying the cDNA sequence comprising SEQ ID NO:1 is pCAMBIA1301.

3. The process for genetic transformation according to claim 2, wherein the cDNA sequence of WsSQS comprising SEQ ID NO:1 is positioned in the plasmid between a promoter and a terminator in pCAMBIA1301.

4. The process for genetic transformation according to claim 3, wherein the promoter is CaMV 35S rRNA (Cauliflower Mosaic virus) and the terminator is Nopaline synthase (Nos).

5. The process for genetic transformation according to claim 1, wherein the tissue exhibits overexpression of WsSQS mRNA transcript levels up to 2-5 fold compared to a respective wild-type tissue.

6. The process for genetic transformation according to claim 1, wherein WsSQS protein activity in transformed root, leaf and stem tissues is 3.3, 2.7 and 2.1 fold higher, respectively, compared to respective wild type tissues.

7. The process for genetic transformation in *Withania somnifera* plants according to claim 1, wherein WsSQS protein activity in the transformed plant is in the range of 50-150 pKat/mg protein.

8. The process for genetic transformation according to claim 1, wherein the secondary metabolites are withanolides selected from the group consisting of withaferin-A, withanolide A and B and withanone.

\* \* \* \* \*